United States Patent [19]

Kimble et al.

[11] Patent Number: 5,087,787
[45] Date of Patent: Feb. 11, 1992

[54] METHOD OF OXIDATIVE CONVERSION

[75] Inventors: James B. Kimble, Bartlesville; John H. Kolts, Ochelata, both of Okla.

[73] Assignee: Phillips Petroleum Company, Bartlesville, Okla.

[21] Appl. No.: 700,092

[22] Filed: May 6, 1991

Related U.S. Application Data

[63] Continuation of Ser. No. 208,830, Jun. 14, 1988, abandoned, which is a continuation of Ser. No. 947,235, Dec. 29, 1986, abandoned.

[51] Int. Cl.$^5$ .............................................. C07C 2/00
[52] U.S. Cl. .................................. 585/500; 585/415; 585/417; 585/541; 585/654; 585/656; 585/700; 585/943
[58] Field of Search ............... 585/500, 943, 415, 417, 585/541, 654, 656, 700

[56] References Cited

U.S. PATENT DOCUMENTS

| | | | |
|---|---|---|---|
| 3,524,819 | 8/1970 | Guerrieri | 252/373 |
| 4,254,293 | 8/1981 | Tremont et al. | 585/500 |
| 4,444,984 | 4/1984 | Jones et al. | 585/500 |
| 4,495,374 | 1/1985 | Jones et al. | 585/500 |
| 4,499,322 | 2/1985 | Jones et al. | 585/500 |
| 4,499,323 | 2/1985 | Gaffney | 585/500 |
| 4,499,324 | 2/1985 | Gaffney | 585/500 |
| 4,517,398 | 5/1985 | Sofranko | 585/500 |
| 4,523,049 | 6/1985 | Jones et al. | 585/500 |
| 4,547,611 | 10/1985 | Jones et al. | 585/943 |
| 4,599,474 | 7/1986 | Devries et al. | 585/943 |
| 4,654,460 | 3/1987 | Kimble et al. | 585/943 |
| 4,658,076 | 4/1987 | Kolts et al. | 585/500 |
| 4,658,077 | 4/1987 | Kolts et al. | 585/500 |

FOREIGN PATENT DOCUMENTS 0189079 7/1986 European Pat. Off. ............ 585/743

OTHER PUBLICATIONS

Chiu-Hsunlin et al., "Oxidative Oxidation of Methane Over Lanthanum Oxide", Journal of Physical Chemistry, vol. 90, No. 4, Feb. 1986, pp. 534–537.
Tomoyasu Ito et al., "Oxidative Dimerization of Methane Over Lithium-Promoted Magnesium Oxide Catalyst", Journal Am. Chem. Soc., vol. 107, 1985, pp. 5062–5068.

*Primary Examiner*—Asok Pal
*Attorney, Agent, or Firm*—K. K. Brandes

[57] ABSTRACT

A method for the oxidative conversion of feed organic compounds to product organic compounds, particularly, the conversion of methane to higher hydrocarbons and the conversion of saturated $C_2$ to $C_7$ hydrocarbons to less saturated hydrocarbons, in which the feed compounds are contacted with a free oxygen-containing gas, water and a contact material, comprising at least one Group IIA metal or lanthanum and oxygen; at least two Group IIA metals, Lanthanum Series metals, zinc, or titanium and oxygen; at least one Group IA metal, at least one Group IIA metal, Lanthanum Series metals, zinc or titanium and oxygen; at least one Group IA metal or Group IIA metal, phosphorous and oxygen; cobalt, at least one of zirconium, zinc, nickel, indium, lead or bismuth, phosphorous, at least one Group IA metal and oxygen; or cobalt, at least one Group IA metal, silicon and oxygen.

20 Claims, No Drawings

METHOD OF OXIDATIVE CONVERSION

This application is a continuation of Ser. No. 208,830, filed June 14, 1988, now abandoned, which is a continuation of Ser. No. 947,235, filed Dec. 29, 1986, now abandoned.

The present invention relates to a method for the oxidative conversion of feed organic materials to product organic materials, in the presence of a free oxygen-containing gas, and reaction-promoting, solid contact materials.

BACKGROUND OF THE INVENTION

Numerous processes are in use and have been proposed for the conversion of organic compounds and feedstocks to more valuable organic compounds and more valuable feedstocks, for use in the organic chemical and petrochemical industries, particularly organic compounds and feedstocks derived from petroleum sources.

One promising approach to such conversion has been the oxidative conversion of organic compounds to other organic compounds. However, in many cases, such oxidative conversion processes are not commercially viable, primarily because they are energy intensive, conversions of the feedstock are low, selectivity to the desired compounds is low and such processes cannot be utilized in a continuous manner. In most of such processes the feedstocks are contacted with a solid contact material. However, there is a difference of opinion among workers in the art concerning the nature of such processes, and, particularly, the function of the contact material and the manner in which such function is performed. For example, workers in the art have, at one time or another, suggested that the function of the contact material involves a purely physical phenomonen, an adsorption-desorption process, either of atomic or molecular oxygen, either on the surface or occluded within the solid material, oxidation-reduction utilizing multivalent metals capable of oxidation-reduction, adsorption and desorption of the organic materials on the solid materials, a free radical mechanism, etc. Consequently, the solid materials utilized are referred to variously as "contact materials", "promoters", "activators" and "catalysts". Accordingly, in order to avoid functional categorization, the terms "solid contact material" or "solid contact materials" will be utilized in the present application.

Since many processes of the prior art are based on the theory that the contact materials function via adsorption-desorption of oxygen, oxidation-reduction, etc., such processes are operated in a cyclic manner by passing an oxidizing gas over the contact material, then contacting the feedstock with the oxygen-containing contact material, and, thereafter, reactivating or regenerating the contact material by again passing an oxidizing gas thereover. Such processes thus require undesirably high temperatures, are energy intensive, since the exothermic and endothermic reactions occur separately, equipment costs are high, because of the necessity for rapid cycling, and the contact material's useful life is comparatively short.

From the above, it is quite clear that the suitability of contact materials for the oxidative conversion of organic compounds is unpredictable. It is, therefore, highly desirable that improved contact materials for such use be developed, and that improved processes utilizing such contact materials be provided, particularly processes which lower the temperatures necessary, lower the energy requirements, are capable of being carried out in a continuous manner, extend the useful life of the contact material, improve the conversion of the feedstock and improve the selectivity to the desired products.

Of the various feedstocks for the organic chemical and petrochemical industries, olefins, such as ethylene and propylene are of particular interest and have become major feedstocks. Of these, ethylene is by far the more important chemical feedstock since the demand for ethylene feedstocks is about double that for propylene feedstocks. Consequently, there is a definite need for materials and processes for the conversion of relatively inexpensive feedstocks to ethylene. At the present time, ethylene is produced almost exclusively by the dehydrogenation or pyrolysis of ethane and propane, naptha and, in some instances, gas oils. About 75% of the ethylene is produced at the present time by steam cracking of ethane and propane derived from natural gas, since natural gas contains from about 5 volume percent to about 60 volume percent of hydrocarbons other than methane, with the majority being ethane. However, relatively severe conditions, particularly temperatures in excess of about 1000° C., are required and, as indicated, such processes are highly energy intensive. In order to reduce the severity of the conditions, particularly temperature, numerous proposals to promote pyrolytic reactions have been made. While some of these processes do, in fact, reduce the severity of the conditions, the conversion of the feedstock and the selectivity to ethylene are still quite low. Of particular interest in this phase of the art, are the oxidative dehydrogenation of alkanes, particularly alkanes having from 2 to 7 carbon atoms, and, still more particularly ethane, and the oxidative conversion of methane to ethylene. However, many of the processes for oxidative dehydrogenation and oxidative conversion of methane, which have been proposed, are subject to some or all of the previously mentioned deficiencies.

More recently, novel contact materials have been discovered which increase the conversion and selectivity to desired products in methods for the oxidative conversion of feed organic compounds to product organic compounds. While this discussion and the discussions hereinafter, at times, refer to certain components of these contact materials as "base materials" and others as "promoters", it is to be understood that these designations are made as a matter of convenience in identification, rather than by way of function. In all instances, the base materials, as well as the promoters, are active components of the contact material and the base materials are not inert "bases" or "carriers", as the designation sometimes indicates or implies.

Commonly assigned U.S. patent applications Ser. Nos. 713,653, 713,756 and 713,674, all filed on Mar. 19, 1985, relate to the use of Group IIA materials as base materials. Likewise, U.S. patent application Ser. No. 713,673, filed Mar. 19, 1985, relates to zinc as a base material. U.S. patent application Ser. No. 742,340, filed June 7, 1985, refers to titanium as a base material. U.S. patent application Ser. No. 742,337, filed June 7, 1985, refers to Lanthanum Series metals as base materials. U.S. patent application Ser. No. 945,129, filed Dec. 22, 1986 relates to certain combinations of these base materials. Each of these base materials is preferably promoted with a Group IA metal promoter. U.S. patent application Ser. No. 742,339, filed June 7, 1985 (now U.S. Pat. No. 4,620,057), relates to contact materials comprising cobalt, a metal selected from the group consisting of zirconium, zinc, nickel, indium, lead and bismuth, phosphorous, at least one Group IA metal and oxygen. Application Ser. No. 742,338, filed June 7, 1985, relates to the use of Group IA and/or Group IIA metal phosphates as contact materials. U.S. patent application Ser. No. 945,223 filed Dec. 22, 1986 relates to the use of a contact material comprising cobalt, at least one Group IA metal, silica and oxygen. All of the above-mentioned contact materials can also be further enhanced by the addition of a halogen thereto. In accordance with U.S. patent application 742,335, filed June 7, 1985, the halogen can be supplied by at least intervally adding the halogen or a halogen precursor to the reaction zone. The entire contents of each of these patent applications and patents are incorporated herein by reference.

While the use of the above-mentioned contact materials and techniques have greatly enhanced the conversion of the feed organic compounds and the selectivity to desired product organic compounds, still further improvement, in both categories, is particularly desirable.

SUMMARY OF THE INVENTION

It is therefore an object of the present invention to provide an improved method for the oxidative conversion of feed organic compounds to product organic compounds which overcomes the above and other disadvantages of the prior art. Another object of the present invention is to provide an improved method for the oxidative conversion of feed organic compounds to product organic compounds which improves the conversion of feed organic compounds and/or the selectivity to product organic compounds. Yet another object of the present invention is to provide an improved method for the oxidative conversion of methane to higher hydrocarbons, particularly ethylene and ethane, which improves the conversion and/or the selectivity to desired products. Yet another object of the present invention is to provide an improved method for the oxidative dehydrogenation of saturated $C_2$ and $C_7$ hydrocarbons to less saturated hydrocarbons, particularly ethane to ethylene, which improves the conversion of feed hydrocarbons and/or the selectivity to desired product hydrocarbons. These and other objects of the present invention will be apparent from the following description.

The conversion of feed organic compounds to product organic compounds and the selectivity to desired product organic compounds are improved, in accordance with the present invention, comprising:

a method for the oxidative conversion of feed organic compounds to product organic compounds, comprising:

contacting said feed organic compounds, a free oxygen-containing gas and water with a solid contact material selected from the group consisting of:

(1) a solid contact material, comprising: (A) a metal selected from the group consisting of a Group IIA metal and lanthanum and (B) oxygen;

(2) a solid contact material, comprising: (A) at least two metals selected from the group consisting of Group IIA metals, Lanthanum Series metals, zinc and titanium and (B) oxygen;

(3) a solid contact material, comprising: (A) at least one metal selected from the group consisting of Group IA metals, (B) at least one metal selected from the group consisting of Group IIA metals, Lanthanum Series metals, zinc and titanium and (C) oxygen;

(4) a solid contact material, comprising: (A) at least one metal selected from the group consisting of Group IA metals and Group IIA metals, (B) phosphorous and (C) oxygen;

(5) a solid contact material, comprising: (A) cobalt, (B) at least one metal selected from the group consisting of zirconium, zinc, nickel, indium, lead and bismuth, (C) phosphorous, (D) at least one metal selected from the group consisting of Group IA metals and (E) oxygen; and (6) a solid contact material, comprising: (A) cobalt, (B) at least one metal selected from the group consisting of Group IA metals, (C) silicon and (D) oxygen, under oxidative conversion conditions sufficient to convert said feed organic compounds to said product organic compounds.

DESCRIPTION OF THE PREFERRED EMBODIMENTS

Processes for the oxidative conversion of feed organic materials to product organic materials, in accordance with the present invention, include the oxidative dehydrogenation of hydrocarbons, particularly alkanes having 2 to 7 carbon atoms, to other hydrocarbons, particularly ethylene, the oxidative conversion of methane to higher hydrocarbons, particularly ethylene, the oxidative methylation of toluene, in the presence of methane, to ethyl benzene and styrene, the oxidative conversion of toluene to stilbene, the oxidative methylation of acetonitrile, in the presence of methane, to acrylonitrile and $C_2+$ hydrocarbons and the oxidative methylation of other hydrocarbons. The solid contact materials of the present invention are particularly useful for the oxidative dehydrogenation of alkane hydrocarbons, having from 2 to 7 carbon atoms, to ethylene, and the oxidative conversion of methane to ethylene, in the presence of a free oxygen-containing gas.

In its broadest aspect, the present invention comprises:

a method for the oxidative conversion of feed organic compounds to product organic compounds, comprising:

contacting said feed organic compounds, a free oxygen-containing gas and water with a solid contact material selected from the group consisting of:

(1) a solid contact material, comprising: (A) a metal selected from the group consisting of a Group IIA metal and lanthanum and (B) oxygen;

(2) a solid contact material, comprising: (A) at least two metals selected from the group consisting of Group IIA metals, Lanthanum Series metals, zinc and titanium and (B) oxygen;

(3) a solid contact material, comprising: (A) at least one metal selected from the group consisting of Group IA metals, (B) at least one metal selected from the group consisting of Group IIA metals, Lanthanum Series metals, zinc and titanium and (C) oxygen;

(4) a solid contact material, comprising: (A) at least one metal selected from the group consisting of Group IA metals and Group IIA metals, (B) phosphorous and (C) oxygen;

(5) a solid contact material, comprising: (A) cobalt, (B) at least one metal selected from the group consisting of zirconium, zinc, nickel, indium, lead and bismuth, (C) phosphorous, (D) at least one metal selected from the group consisting of Group IA metals and (E) oxygen; and (6) a solid contact material, comprising: (A) cobalt, (B) at least one metal selected from the group consisting of Group IA metals, (C) silicon and (D) oxygen, under oxidative conversion conditions sufficient to convert said feed organic compounds to said product organic compounds.

In a preferred embodiment, the contact materials are selected from the group consisting of:

(1) a solid contact material, consisting essentially of: (A) a metal selected from the group consisting of a Group IIA metal and lanthanum and (B) oxygen;

(2) a solid contact material, consisting essentially of: (A) at least two metals selected from the group consisting of Group IIA metals, Lanthanum Series metals, zinc and titanium and (B) oxygen;

(3) a solid contact material, consisting essentially of: (A) at least one metal selected from the group consisting of Group IA metals, (B) at least one metal selected from the group consisting of Group IIA metals, Lanthanum Series metals, zinc and titanium and (C) oxygen;

(4) a solid contact material, consisting essentially of: (A) at least one metal selected from the group consisting of Group IA metals and Group IIA metals, (B) phosphorous and (C) oxygen;

(5) a solid contact material, consisting essentially of: (A) cobalt, (B) at least one metal selected from the group consisting of zirconium, zinc, nickel, indium, lead and bismuth, (C) phosphorous, (D) at least one metal selected from the group consisting of Group IA metals and (E) oxygen; and (6) a solid contact material, consisting essentially of: (A) cobalt, (B) at least one metal selected from the group consisting of Group IA metals, (C) silicon and (D) oxygen.

Preferred Group IA metals utilized in the contact materials are selected from the group consisting of lithium, sodium and potassium.

Preferred Group IIA metals are selected from the group consisting of magnesium, calcium, strontium and barium.

Lanthanum Series metals are preferably selected from the group consisting of lanthanum, praseodymium, samarium and terbium. Lanthanum is preferred.

Contact material (5) preferably includes zirconium. When a Group IA metal is utilized in this contact material, it is preferably selected from the group consisting of lithium, sodium and potassium, preferably sodium, and still more preferably, both sodium and potassium.

Contact material (6) preferably contains lithium, as a Group IA metal, and still more preferably, a combination of lithium and sodium.

All of the subject contact materials may also contain halogen ions, or compounds containing halogen ions, as a component, preferably chlorine.

Contact materials (1), (2), (3) and (6) may also contain phosphorous, or compounds containing phosphorous, as a component and contact material (6) preferably contains both phosphorous and a halogen.

Contact materials (5) and (6) may also optionally contain sulfur or a compound containing sulfur.

While the exact compositions and nature of the contact materials are not known, it is believed that, irrespective of the starting materials, the components are converted to their oxide form during calcination. Accordingly, with the exception of phosphorous, it is believed that all components are present as oxides or mixed oxides. It is believed that phosphorous is present as a phosphate. Where a halogen is present, it is believed that the halogen is present as a halide. Where sulfur is present, it is believed that it is present as a sulfate. By the same token, it is not known what changes the contact materials go through during the course of a reaction, and it is possible that oxides may be converted to carbonates, and that like changes may take place with reactants, products or by-products.

The contents and relative proportions of the various components of the contact materials do not appear to be highly critical in most cases. Accordingly, when the term "effective amount" is utilized, with reference to the content of the components of the contact materials herein, this term is meant to include more than an insignificant amount and, thus, a small amount sufficient to effect the function of the contact material for the purpose for which it is utilized. Accordingly, any of the components of the contact materials may be present in amounts anywhere from an effective amount to near 100 percent, for example, between about 0.05 and 99.95 weight percent, expressed in terms of the elemental metal based on the total weight of the contact material. This is particularly true of the materials referred to herein as "base" materials in contact materials (1), (2) and (3), and the cobalt of contact material (6). Most importantly, such amounts or proportions apply when the contact material contains two or more of the base materials in combination, since a small amount of one base material can be utilized and is effective in improving the contact material when mixed with an extremely large amount of a second base material. However, preferred contact materials do contain certain compounds in major proportions, and other compounds in minor proportions, and it is for this reason that certain compounds are referred to as "base" materials, while others are referred to as "promoters".

Where Group IA and/or Group IIA metals are utilized in contact materials (1), (2), (3), (4) or (5) and they are not in the form of electrically balanced compounds with the base or major component, such Group IA and Group IIA metals are preferably utilized in minor amounts, usually between about 0.1 and 50 weight percent, still more preferably, between about 0.5 and 15 weight percent, and optimally, between about 1 weight percent and about 5 weight percent, expressed in terms of the elemental metal based on the total weight of the contact material. Halogens are also preferably utilized in minor amounts, usually between about 0.1 weight percent and 5 weight percent, expressed as elemental halogen based on the total weight of the contact material. In contact material (5), the cobalt and the metal selected from the group consisting of zirconium, zinc, niobium, indium, lead and bismuth are utilized as major components, while the remaining components are utilized in minor amounts. By way of example, the preferable atomic ratio of cobalt to the metals selected from the group consisting of zirconium, zinc, niobium, indium, lead and bismuth is in the range of about 1/1 to about 20/1 and more preferably, in the range of about 3/1 to 6/1.

The phosphorous in all contact materials is preferably present in an amount of about 1 weight percent to about 10 weight percent and more preferably, between about 2 weight percent and about 5 weight percent, expressed in terms of phosphorous oxide based on the total weight of the contact material. Preferably, the alkali metal of contact material (5) is present in concentrations of about 1 weight percent to about 10 weight percent and more preferably, between about 2 weight percent and about 5 weight percent, also expressed in terms of alkali metal oxide based on the total weight of the contact material. Preferred concentrations of sulfur are in the range of about 1 weight percent to about 10 weight percent and, more preferably, between about 2 weight percent and about 5 weight percent, expressed in terms of elemental sulfur based on the total weight of the contact material. The halogen in contact material (5) is preferably present in an amount between about 1 weight percent and about 10 weight percent and, more preferably, between about 2 weight percent and about 5 weight percent, expressed in terms of elemental halogen based on the total weight of the contact material.

In contact material (6), the amounts of some of the components do appear to be somewhat critical. As previously indicated, the amount of cobalt may range from an effective amount to near 100 percent. However, due to the expense and difficulty of obtaining cobalt, it is preferred that the cobalt be present in amounts between about 0.05 and 50 weight percent, preferably, 0.05 to 20 weight percent, and, still more preferably, between about 0.05 and 10 weight percent, again expressed in terms of elemental cobalt based on the total weight of the catalyst. The same principles apply to the content of alkali metals, phosphorous, halogen and sulfur, as applied to the previously discussed contact materials. However, the alkali metals other than sodium are preferably present in amounts between about 0.01 and 30 weight percent, and, still more preferably, between about 0.05 and 15 weight percent, expressed in terms of elemental alkali metal based on the total weight of the catalyst. Sodium may also be utilized in these amounts but, preferably, when utilized in combination with another alkali metal, particularly lithium, the sodium should be present in amounts between about 0.05 and 1.0 weight percent and more preferably, between about 0.05 and 0.8 weight percent. The balance of this contact material is, of course, silicon in the form of silica. In any event, the base materials of contact materials (1), (2) and (3), the combination of cobalt and zirconium, zinc, nickel, indium, lead or bismuth of contact material (5), and the silica of contact material (6) are all preferably present in amounts of at least 50 weight percent, with the total content of the other components, or promoters, being less than about 50 percent.

The above-mentioned components can be mixed with or deposited on an "inert support material" adapted to harden or support the active materials. The term "inert support material", when utilized in this context, is meant to include any material which does not react with or exchange ions with the active components, has no significant functional effect on the production of desired or undesired products in the process for which the solid contact material is utilized, and functions only as a hardening agent or support for the active components. Where such solid support material is utilized, the weight of such solid support material is not included in the relative weights of the active components set forth above.

The components of the contact material can be derived from any suitable source of such materials, such as carbonates, oxides, hydroxides, nitrates, octoates, chlorides, phosphates, sulfides and sulfonates, of an organic or inorganic nature. The contact materials can be prepared by any suitable method, known in the art, for the preparation of such materials in solid form. Particularly effective techniques are those utilized for the preparation of solid catalysts. Conventional methods include coprecipitation from an aqueous, an organic or a combination solution-dispersion, impregnation, dry mixing, wet mixing or the like, alone or in various combinations. In general, any method can be used which provides compositions of matter containing the prescribed components in effective amounts. When slurries, precipitates or the like are prepared, they will generally be dried, usually at a temperature sufficient to volatilize the water or other carrier, such as about 220° F. to about 450° F. In all cases, irrespective of how the components are combined and irrespective of the source of the components, the dried composition is calcined in the presence of a free oxygen-containing gas, usually at temperatures between about 600° F. and about 1500° F. for from 1 to about 24 hours. As pointed out hereinafter, contact material (5) can be calcined in a reducing or inert atmosphere or an oxygen-containing atmosphere.

The manner in which the contact materials of the present invention perform the reaction-promoting function is not fully understood. Accordingly, the present invention is not to be limited to any particular theory. However, several significant observations have been made in parallel work and in accordance with the present invention.

First, each of the components of contact materials (1), (2), (3), (4), (5) and (6), unless designated as optional, appear necessary and participate in the reaction promoting function thereof. Hence, simply because a particular component is present in an minor amount it cannot be categorized as a "promoter" or "active" component and the components present in major proportions cannot be categorized as inert "bases", "carriers" or "supports".

Secondly, the contact materials do not promote oxidative conversion reactions or result in insignificant conversion of feed organic materials and/or insignificant selectivity to product organic compounds in the absence of a free oxygen-containing gas.

Finally, it has been observed, in accordance with the present invention, that contact material (5) results in very poor conversion and/or selectivity, if it is in a high state of oxidation, and reduction of the state of oxidation is highly desirable.

Based on these observations, it can be concluded that, irrespective of whether multivalent components are present in the contact materials, the reaction mechanism of the present invention is not oxidation-reduction. Accordingly, at least when the reactions are carried out in the presence of a free oxygen-containing gas, in accordance with the present invention, it is not necessary that the contact material include multivalent components capable of undergoing oxidation-reduction or redox reactions, as taught by many workers in prior art.

It has also been found, in accordance with the present invention, that the halogen of the contact materials becomes depleted during the course of oxidative conversion in the presence of a free oxygen-containing gas. Accordingly, when carrying out the oxidative conversion reaction, in accordance with the present invention, a material containing at least one halogen, or halogen precursor, such as gaseous halogen, for example, chlorine, methylchloride, methylenechloride and like compounds of the other halogens, is at least intervally contacted with the contact material. The material containing the halogen is preferably a normally gaseous material or will be in a vapor state under the operating conditions of the oxidative conversion reaction. In any event, in accordance with the present invention, the reaction-promoting activity of the contact material can be maintained throughout the conduct of the method by continuously adding the material containing the halogen to the organic feed compounds and free oxygen-containing gas, or by adding the material containing the halogen at intervals during the conduct of the method. In the latter case, the flow of feed organic compounds and free oxygen-containing gas can be discontinued during the addition of the material containing the halogen, although this is not necessary.

The state of oxidation of solid contact materials (1), (2), (3), (4) and (6) does not appear to be critical and, normally, it is not necessary to contact any of these contact materials with a reducing agent in order to maintain their reaction-promoting activity. However, when these contact materials have been utilized in long production runs, occasional contacting of the contact material with a reducing agent may be beneficial. On the other hand, as indicated previously, the reaction-promoting effect of solid contact material (5) does appear to be affected by the degree of oxidation thereof. It has been found that, after a period of use, in the presence of a free oxygen-containing gas, there is a tendency for this contact material to become "overoxidized" and lose its reaction-promoting activity. However, in accordance with the present invention, it has been found that the reaction-promoting activity of this contact material can be maintained at near its peak activity by intervally contacting the solid contact material with a material containing at least one reducing agent.

It has also been discovered that the solid contact materials of the present invention can be prepared without, or with only small amounts of the halogen component, and such component can be added by, thereafter, treating the calcined contact material with a material containing at least one halogen, or halogen precursor, preferably in a gaseous or vapor state. Such treatment can be preformed prior to disposing the contact material in the reaction zone in which the oxidative conversion reaction is to be carried out, but, preferably the calcined contact material is disposed in the reaction zone and treated with the halogen prior to the introduction of the organic feed material and free oxygen-containing gas, or along with the first portion of the organic feed and oxygen. This technique also results in more active contact materials, since it has also been found that, in at least some cases, it is difficult to incorporate an effective amount of halogen in the contact material during preparation and/or retain an effective amount of halogen in the contact material during preparation, particularly during calcining.

Contact material (5), as previously indicated, has another peculiarity, namely, that it produces substantially superior results if it is in a lower state of oxidation. Normally, in the preparation of this contact material, the combined components are dried in the presence of a free oxygen-containing gas, usually air. As a result of the presence of the air at an elevated temperature, it is believed that at least some of the components of the contact material are in a high state of oxidation after drying and, therefore, are inefficient contact materials for the oxidative conversion reaction. Consequently, it has been the past practice to calcine the dried contact material in an inert or reducing atmosphere in order to reduce the oxidation level of the material. This, of course, is difficult and adds the expense of preparation. In accordance with the present invention, it has been found that the combined air-dried components of the contact material may be calcined in a conventional manner in the presence of a free oxygen-containing gas, usually air, and, thereafter, pretreated, to reduce the level of oxidation, by contacting the calcined contact material with a material, including at least one reducing material. Suitable reducing materials include hydrogen and lower alkanes such as methane, ethane, etc. This technique is even more convenient, to the extent that the preferred technique involves disposing a calcined contact material in the reactor in which the oxidative conversion reaction is to be carried out for the pretreatment with the reducing agent and, when methane or ethane are starting materials for the oxidative conversion reaction, such materials are already conveniently available. Contact material (5) can also be prepared without halogen, or with only a small amount of halogen, and the halogen also added during the pretreatment. Consequently, the pretreatment comprises contacting the air calcined contact material with both a material containing at least one halogen and a material containing a reducing agent. Such contacting may be simultaneous or in either sequence.

The present invention can best be illustrated by the following examples of the oxidative conversion of methane to ethylene.

In addition to methane, the hydrocarbon feedstock, employed in the conversion of methane to ethylene, may contain other hydrocarbon or non-hydrocarbon components. The presence of ethane, propane and the like is not detrimental. It has been found that carbon dioxide and water are not detrimental, since they are often products of the process. However, it is to be noted that, while water is a by-product of the reaction, the water added in accordance with the present invention is in addition to produced water and is a component of the feed. It has also been found that inert gases, such as nitrogen, helium and the like are not detrimental. Consequently, the method of the present invention can effectively utilize any conventional natural gas. To the extent that significant amounts of hydrogen sulfide are present in the natural gas, it is desirable to first remove the hydrogen sulfide, since it is believed that excessive amounts of this material can be detrimental to the method. Accordingly, a relatively inexpensive source of methane, namely natural gas, can be employed without expensive separation or processing of the components thereof, with the exception of the relatively inexpensive removal of excess amounts of hydrogen sulfide. Other sources of methane or methane-containing gases can also be utilized.

The free oxygen-containing gas may be any suitable oxygen-containing gas, such as oxygen, oxygen-enriched air or air. The method of the present application has been effectively carried out utilizing air as a source of oxygen.

The volumetric ratio of methane to free oxygen should be in excess of about 1/1, preferably it is between about 1/1 and about 30/1, and still more preferably, between about 4/1 and about 15/1. It has been found that a ratio of methane to free oxygen of at least about 1/1 is necessary, in accordance with the present invention, in order to obtain maximum conversion of methane and high selectivity to higher hydrocarbons, particularly ethylene. The volumetric ratio of water to $CH_4$ is between about 0.25/1 and 30/1 and preferably, between 0.25/1 and 10/1, expressed in terms of the gaseous or vapor phase.

It has been found that the method can be carried out between two extremes, namely, low conversion of methane/high selectivity to higher hydrocarbons, particularly ethylene, and high conversion of methane/low selectivity to the higher hydrocarbons, particularly ethylene. The process parameters (space velocity, temperature, and reactant partial pressure) can, to some extent, be used to control the reaction at the desired point between these two limits. Consequently, the reaction conditions may vary between broad limits.

The temperature is preferably at least about 500° C. and will generally vary between about 500° C. and about 1500° C. However, in order to obtain high conversions of methane and high selectivities to ethylene and ethane, the temperature is preferably between about 500° C. and about 900° C. and most desirably between about 600° C. and about 800° C.

It has also been found that, as the partial pressure of oxygen is increased, the selectivity to higher hydrocarbons decreases and the selectivity to carbon dioxide increases and vice versa. Total pressures may vary anywhere from around 1 atmosphere to about 1500 psi but are preferably below about 300 psi and ideally below about 100 psi.

Methane flow rates can also vary over a wide range, for example, from 0.5 to 100 cubic centimeters per minute per cubic centimeter of contact material. Preferably, however, the rate is between about 1.0 and about 75 cubic centimeters per minute per cubic centimeter of contact material.

The total flow velocities of all gaseous materials, including diluents, through a fixed bed reactor, may be at any rate effective for the oxidative conversion reaction. For example from 50 to 10,000 GHSV and preferably from 500 to 5000 GHSV.

In addition to the high conversion of methane and high selectivity to ethylene and ethane attainable, the contact materials are not readily poisoned and will tolerate the presence of carbon dioxide, carbon monoxide and the like. In addition, the contact materials appear to be long lived. Concomitantly, the process can be carried out continuously in fixed, moving, fluidized, ebullating or entrained bed reactors.

A contact material comprising lithium oxide on a magnesium oxide base is representative of the contact materials referred to in the present application and functions as a contact material in all of the oxidative conversion processes referred to. Consequently, this contact material was utilized in the examples. The contact material was prepared by slurrying magnesium oxide with sufficient lithium carbonate to produce a contact material containing 3 weight percent lithium based on the total weight of the contact material. The slurry was dried and thereafter calcined at 800° C. for 8 hours. The following table sets forth the conditions under which methane was converted to ethane and ethylene and the results thereof.

DILUENT EFFECTS
GHSV-10, Temperature-700° C.
Feed: $CH_4$-208 cc/min
$O_2$-42 cc/min
Dil.-166 cc/min

| Diluent | Conv | Selectivity | | $C_2=/C_2$ |
|---|---|---|---|---|
| | | Ethane | Ethylene | |
| $CH_4$ | 11.8 | 35.2 | 31.4 | 0.89 |
| $N_2$ | 16.3 | 32.5 | 32.8 | 1.01 |
| $H_2O$ | 19.9 | 29.7 | 35.7 | 1.20 |

EFFECT OF $H_2O$, INCREASING GHSV
Temperature-700° C.
Feed: $CH_4$-208 cc/min
$O_2$-42 cc/min

| $H_2O$ Flow | $H_2O/CH_4$ | Conv | Selectivity | | $C_2=/C_2$ |
|---|---|---|---|---|---|
| | | | Ethane | Ethylene | |
| 0 | 0.0 | 16.5 | 27.3 | 32.7 | 1.20 |
| 52 | 0.25 | 18.2 | 27.8 | 34.6 | 1.24 |
| 104 | 0.5 | 19.1 | 28.5 | 35.2 | 1.23 |
| 166 | 0.8 | 19.6 | 30.0 | 36.0 | 1.20 |
| 228 | 1.0 | 20.0 | 30.7 | 35.8 | 1.17 |
| 416 | 2.0 | 19.5 | 35.6 | 35.1 | 0.99 |
| 832 | 4.0 | 18.0 | 41.2 | 32.9 | 0.80 |

EFFECT OF $H_2O$ AT CONSTANT GHSV
GHSV-1000, Temperature-700° C.
Feed: $CH_4/O_2$--5/1

| $CH_4$ Flow | $H_2O/CH_4$ | Conv | Selectivity | | $C_2=/C_2$ |
|---|---|---|---|---|---|
| | | | Ethane | Ethylene | |
| 347 | 0.00 | 15.7 | 30.6 | 31.2 | 1.01 |
| 287 | 0.25 | 18.2 | 29.1 | 33.5 | 1.15 |
| 245 | 0.50 | 19.5 | 28.9 | 34.6 | 1.20 |
| 208 | 0.80 | 20.9 | 28.5 | 36.1 | 1.27 |
| 189 | 1.00 | 21.1 | 29.0 | 36.9 | 1.27 |
| 130 | 2.00 | 23.0 | 29.0 | 38.8 | 1.34 |
| 80 | 4.00 | 23.7 | 29.7 | 40.6 | 1.37 |

It is to be observed from the above example that the presence of water, which, of course, is in the form of steam during the reaction, increases the conversion of methane and the selectivity to ethylene and ethane, particularly, ethylene, while at the same time reducing the selectivity to carbon monoxide and carbon dioxide, which are the main by-product components of the product gas.

Conditions for the oxidative dehydrogenation of $C_2$ to $C_7$ hydrocarbons can also vary over the same broad ranges useful for the oxidative conversion of methane to higher hydrocarbons and can be optimized by one skilled in the art by conventional, routine experimentation.

As a general rule, the conditions for the oxidative dehydrogenation of $C_2$ to $C_7$ hydrocarbons will fall within the lower part of the ranges previously specified for the oxidative conversion of methane to higher hydrocarbons. For example, a GHSV of 100 to 1000, and preferably 400 to 500, a hydrocarbon to oxygen ratio of 1/1 to 30/1, and preferably 1/1 to 3/1, a temperature of 600° to 775° C., and preferably 650° to 725° C., and a pressure of 0.5 to 10 atmospheres, and preferably 1 atmosphere, are highly effective. The volumetric ratio of water to hydrocarbon is between about 0.25/1 and 30/1 and preferably between about 0.25/1 and 10/1.

While specific materials, conditions of operation, modes of operation and equipment have been referred That which is claimed is:

1. A method for the oxidative conversion of feed organic compounds comprising methane to product organic compounds comprising higher hydrocarbons, comprising:
   contacting said feed organic compounds, a free oxygen-containing gas and water
   with at least one solid contact material selected from the group consisting of a solid contact material consisting essentially of lanthanum oxide and solid contact materials comprising (a) at least one promoter comprising a metal selected from the group consisting of lithium and sodium and (b) at least one base material selected from the group consisting of magnesium oxide, calcium oxide, lanthanum oxide and samarium oxide,
   under oxidative conversion conditions sufficient to convert said feed organic compounds to said product organic compounds.

2. A process in accordance with claim 1, wherein said solid contact material consists essentially of lanthanum oxide.

3. A process in accordance with claim 1, wherein said solid contact material consists essentially of at least one lithium-containing promoter and magnesium oxide as base material.

4. A process in accordance with claim 3, wherein the lithium content in said solid contact material is in the range of about 0.5 to about 15 weight percent Li.

5. A process in accordance with claim 3, wherein said solid contact material consists essentially of lithium oxide and magnesium oxide.

6. A process in accordance with claim 5, wherein the lithium content in said solid contact material is in the range of about 1 to about 5 weigh percent Li.

7. A process in accordance with claim 5, wherein said solid contact material has been prepared by forming a slurry of magnesium oxide with lithium carbonate, and thereafter drying and calcining said slurry.

8. A process in accordance with claim 11, wherein said solid contact material consists essentially of a lithium-containing promoter and calcium oxide as base material.

9. A process in accordance with claim 8, wherein the lithium content in said solid content material is in the range of about 0.5 to about 15 weight-% Li.

10. A process in accordance with claim 1, wherein said solid contact material consists essentially of a sodium-containing promoter and magnesium oxide as base material.

11. A process in accordance with claim 10, wherein the sodium content in said solid contact material is int h range of about 0.5 to about 15 weight-% Na.

12. A process in accordance with claim 11, wherein said solid contact material consists essentially of a sodium-containing promoter and calcium oxide as base material.

13. A process in accordance with claim 12, wherein the sodium content in said solid contact material is about 0.5 to about 15 weight-% Na.

14. A process in accordance with claim 11, wherein said solid contact material consists essentially of said at least one alkali metal-containing promoter and at least one base material selected from the group consisting of lanthanum oxide and samarium oxide.

15. A process in accordance with claim 14, wherein the alkali metal content is said solid contact material is in he range of about 0.5 to about 15 weight percent.

16. A process in accordance with claim 11, wherein the volumetric ratio of methane to free oxygen is in the range of about 1:1 to about 30:1.

17. A process in accordance with claim 11, wherein the volumetric ratio of gaseous water to methane is in the range of about 0.25:1 to about 30:1.

18. A process in accordance with claim 17, wherein said volumetric ratio is in the range of about 0.25:1 to about 10:1.

19. A process in accordance with claim 1, wherein said contacting is carried out at a temperature in the range of about 500° C. to about 900° C.

20. A process in accordance with claim 1, wherein at least one halogen containing material is present during said contacting.

* * * * *